(12) United States Patent
Streeter

(10) Patent No.: US 9,211,085 B2
(45) Date of Patent: Dec. 15, 2015

(54) RESPIRATION SENSING SYSTEM

(75) Inventor: Richard B. Streeter, Andover, MA (US)

(73) Assignee: Foster-Miller, Inc., Waltham, MA (US)

( * ) Notice: Subject to any disclaimer, the term of this patent is extended or adjusted under 35 U.S.C. 154(b) by 510 days.

(21) Appl. No.: 12/799,822

(22) Filed: May 3, 2010

(65) Prior Publication Data

US 2011/0270115 A1 Nov. 3, 2011

(51) Int. Cl.
*A61B 5/08* (2006.01)
*A61B 5/00* (2006.01)
*A61B 5/0402* (2006.01)

(52) U.S. Cl.
CPC ............ *A61B 5/0816* (2013.01); *A61B 5/6823* (2013.01); *A61B 5/6831* (2013.01); *A61B 5/0402* (2013.01)

(58) Field of Classification Search
CPC .. A61B 5/0816; A61B 5/0402; A61B 5/6831; A61B 5/6823
USPC ................. 600/388, 529–543; 442/79, 85, 86
See application file for complete search history.

(56) References Cited

U.S. PATENT DOCUMENTS

| | | | |
|---|---|---|---|
| 2,021,111 A | 11/1935 | Wheat | |
| 2,953,970 A | 9/1960 | Maynard | |
| 2,963,535 A | 12/1960 | Wegener et al. | |
| 2,963,538 A | 12/1960 | Dahlgren | |
| 2,997,521 A | 8/1961 | Dahlgren | |
| 3,086,071 A | 4/1963 | Preston | |
| 3,229,030 A | 1/1966 | Baermann | |
| 3,247,755 A | 4/1966 | Siegmund | |
| 3,288,175 A | 11/1966 | Valko | |
| 3,371,250 A | 2/1968 | Ross et al. | |
| 3,414,666 A | 12/1968 | Doundoulakis et al. | |
| 3,447,120 A | 5/1969 | Rask et al. | |
| 3,473,872 A | 10/1969 | Okamura | |
| 3,476,870 A | 11/1969 | Ross | |
| 3,479,565 A | 11/1969 | Ross et al. | |
| 3,495,025 A | 2/1970 | Ross | |
| 3,507,321 A | 4/1970 | Palma | |
| 3,551,585 A | 12/1970 | Smart et al. | |
| 3,627,903 A | 12/1971 | Plummer | |
| 3,631,298 A | 12/1971 | Davis | |
| 3,654,380 A | 4/1972 | Tatum et al. | |
| 3,700,538 A | 10/1972 | Kennedy | |
| 3,711,627 A | 1/1973 | Maringulov | |
| 3,778,331 A | 12/1973 | Scharf | |

(Continued)

FOREIGN PATENT DOCUMENTS

DE 103 06 953 A1 10/2003
EP 0320901 A2 6/1989

(Continued)

OTHER PUBLICATIONS

WS Hampshire. "Teflon Properties."*

(Continued)

*Primary Examiner* — Patricia Mallari
*Assistant Examiner* — Tiffany Weston
(74) *Attorney, Agent, or Firm* — Iandiorio Teska & Coleman, LLP

(57) ABSTRACT

A respiration sensing subsystem includes a band made of stretchable material and a pair of spaced conductors extending along the band in a flexible pattern. A moisture repellant compound is added to the stretchable material of the band between the pair of spaced conductors.

6 Claims, 2 Drawing Sheets

(56) References Cited

U.S. PATENT DOCUMENTS

| | | |
|---|---|---|
| 3,878,316 A | 4/1975 | Groff |
| 3,882,846 A | 5/1975 | Fletcher et al. |
| 3,891,011 A | 6/1975 | Tisdale et al. |
| 3,909,508 A | 9/1975 | Ross |
| 3,926,360 A | 12/1975 | Moister, Jr. |
| 3,984,622 A | 10/1976 | Ross |
| 4,031,284 A | 6/1977 | Ingraham |
| 4,034,150 A | 7/1977 | Burnett, III |
| 4,035,694 A | 7/1977 | Barton et al. |
| 4,095,042 A | 6/1978 | Ross |
| 4,103,102 A | 7/1978 | Klein |
| 4,106,677 A | 8/1978 | Helmso et al. |
| 4,111,510 A | 9/1978 | Zurcher |
| 4,143,236 A | 3/1979 | Ross et al. |
| 4,145,030 A | 3/1979 | Ingraham |
| 4,150,464 A | 4/1979 | Tracy |
| 4,158,103 A | 6/1979 | Danilin et al. |
| 4,158,104 A | 6/1979 | Ross |
| 4,159,394 A | 6/1979 | Ross |
| 4,171,555 A | 10/1979 | Bakker et al. |
| 4,191,800 A | 3/1980 | Holtzman |
| 4,196,355 A | 4/1980 | Maine |
| 4,227,520 A | 10/1980 | Lord |
| 4,229,615 A | 10/1980 | Orr, Jr. et al. |
| 4,249,267 A | 2/1981 | Voss |
| 4,254,951 A | 3/1981 | DeLaney |
| 4,281,211 A | 7/1981 | Tatum et al. |
| 4,281,237 A | 7/1981 | Berenson |
| 4,370,658 A | 1/1983 | Hill |
| 4,373,534 A | 2/1983 | Watson |
| 4,430,384 A | 2/1984 | George |
| 4,442,314 A | 4/1984 | Piper |
| 4,452,847 A | 6/1984 | Siemon |
| 4,460,803 A | 7/1984 | Piper |
| 4,463,323 A | 7/1984 | Piper |
| 4,504,696 A | 3/1985 | Piper |
| 4,513,055 A | 4/1985 | Leibowitz |
| 4,527,135 A | 7/1985 | Piper |
| 4,550,411 A | 10/1985 | Stonestreet et al. |
| 4,559,411 A | 12/1985 | Piper |
| 4,572,197 A | 2/1986 | Moore et al. |
| 4,590,623 A | 5/1986 | Kitchman |
| 4,658,089 A | 4/1987 | Guzy et al. |
| 4,670,351 A | 6/1987 | Keane et al. |
| 4,682,828 A | 7/1987 | Piper et al. |
| 4,684,762 A | 8/1987 | Gladfelter |
| 4,709,397 A | 11/1987 | Voshall et al. |
| 4,712,298 A | 12/1987 | Mondor, III |
| 4,723,925 A | 2/1988 | Orr, Jr. et al. |
| 4,735,847 A | 4/1988 | Fujiwara et al. |
| 4,741,707 A | 5/1988 | Mondor, III |
| 4,746,769 A | 5/1988 | Piper |
| 4,753,088 A | 6/1988 | Harrison et al. |
| 4,761,005 A | 8/1988 | French et al. |
| 4,774,434 A | 9/1988 | Bennion |
| 4,803,096 A | 2/1989 | Kuhn et al. |
| 4,804,806 A | 2/1989 | Orr, Jr. et al. |
| 4,807,640 A | 2/1989 | Watson et al. |
| 4,808,771 A | 2/1989 | Orr, Jr. |
| 4,814,585 A | 3/1989 | Klein |
| 4,815,473 A | 3/1989 | Watson et al. |
| 4,817,625 A | 4/1989 | Miles |
| 4,827,943 A | 5/1989 | Bornn et al. |
| 4,851,613 A | 7/1989 | Jacques |
| 4,854,446 A | 8/1989 | Strader |
| 4,856,837 A | 8/1989 | Hammersla, Jr. |
| 4,868,565 A | 9/1989 | Mettes et al. |
| 4,875,144 A | 10/1989 | Wainwright |
| 4,877,646 A | 10/1989 | Kuhn et al. |
| 4,910,358 A | 3/1990 | Mittelbusher |
| 4,912,611 A | 3/1990 | Lyle |
| 4,913,978 A | 4/1990 | Klotz et al. |
| 4,930,517 A | 6/1990 | Cohen et al. |
| 4,948,951 A | 8/1990 | Balzano |
| 4,960,118 A | 10/1990 | Pennock |
| 4,983,452 A | 1/1991 | Daimon et al. |
| 4,992,335 A | 2/1991 | Guerra et al. |
| 5,008,517 A | 4/1991 | Brekkestran et al. |
| 5,032,705 A | 7/1991 | Batcheller et al. |
| 5,047,788 A | 9/1991 | Gillard |
| 5,073,984 A | 12/1991 | Tone et al. |
| 5,076,801 A | 12/1991 | Schroll |
| 5,089,669 A | 2/1992 | Piper et al. |
| 5,095,628 A | 3/1992 | McKenney et al. |
| 5,103,504 A | 4/1992 | Dordevic |
| 5,104,726 A | 4/1992 | Ross |
| 5,119,020 A | 6/1992 | Massey et al. |
| 5,126,920 A | 6/1992 | Cardashian et al. |
| 5,140,131 A | 8/1992 | Macher et al. |
| 5,191,893 A | 3/1993 | Reiten |
| 5,203,717 A | 4/1993 | Beck et al. |
| 5,241,300 A | 8/1993 | Buschmann |
| 5,259,792 A | 11/1993 | Beck et al. |
| 5,277,617 A | 1/1994 | Shasteen |
| 5,295,490 A | 3/1994 | Dodakian |
| 5,301,678 A | 4/1994 | Watson et al. |
| 5,316,830 A | 5/1994 | Adams, Jr. et al. |
| 5,318,845 A | 6/1994 | Tanaka et al. |
| 5,331,115 A | 7/1994 | Ysbrand |
| 5,332,869 A | 7/1994 | Hagiwara |
| 5,342,204 A | 8/1994 | Och |
| 5,357,593 A | 10/1994 | Bossler |
| 5,362,656 A | 11/1994 | McMahon |
| 5,371,326 A | 12/1994 | Clearwaters-Dreager et al. |
| 5,373,103 A | 12/1994 | Orr, Jr. et al. |
| 5,380,954 A | 1/1995 | Orr, Jr. |
| 5,387,113 A | 2/1995 | Dickerson et al. |
| 5,393,928 A | 2/1995 | Cribb et al. |
| 5,415,561 A | 5/1995 | Mavrin et al. |
| 5,457,610 A | 10/1995 | Benardoni et al. |
| 5,499,927 A | 3/1996 | Ohno et al. |
| 5,502,631 A | 3/1996 | Adachi |
| 5,523,528 A | 6/1996 | Bese et al. |
| 5,531,405 A | 7/1996 | Goldberg |
| 5,532,429 A | 7/1996 | Dickerson et al. |
| 5,538,781 A | 7/1996 | Rao et al. |
| 5,543,585 A | 8/1996 | Booth et al. |
| 5,600,098 A | 2/1997 | Kazaks |
| 5,674,752 A | 10/1997 | Buckley et al. |
| 5,680,681 A | 10/1997 | Fuss |
| 5,691,062 A | 11/1997 | Shalaby et al. |
| 5,701,370 A | 12/1997 | Muhs et al. |
| 5,730,145 A | 3/1998 | Defares et al. |
| 5,747,101 A | 5/1998 | Booth et al. |
| 5,749,365 A | 5/1998 | Magill |
| 5,760,340 A | 6/1998 | Orr, Jr. et al. |
| 5,763,058 A | 6/1998 | Isen et al. |
| 5,769,755 A | 6/1998 | Henry et al. |
| 5,773,762 A | 6/1998 | Orr, Jr. et al. |
| 5,774,341 A | 6/1998 | Urbish et al. |
| 5,786,977 A | 7/1998 | Cohen |
| 5,788,528 A | 8/1998 | Orr, Jr. et al. |
| 5,798,907 A | 8/1998 | Janik |
| 5,802,607 A | 9/1998 | Triplette |
| 5,824,996 A | 10/1998 | Kochman et al. |
| 5,829,987 A | 11/1998 | Fritsch et al. |
| 5,832,296 A | 11/1998 | Wang et al. |
| 5,834,693 A | 11/1998 | Waddell et al. |
| 5,837,624 A | 11/1998 | Sakaguchi et al. |
| 5,876,430 A | 3/1999 | Shoberg et al. |
| 5,883,364 A | 3/1999 | Frei et al. |
| 5,906,004 A | 5/1999 | Lebby et al. |
| 5,911,595 A | 6/1999 | Orr, Jr. et al. |
| 5,912,653 A | 6/1999 | Fitch |
| 5,913,830 A | 6/1999 | Miles |
| 5,914,585 A | 6/1999 | Grabon |
| 5,914,660 A | 6/1999 | Mesibov et al. |
| 5,919,141 A | 7/1999 | Money et al. |
| 5,926,144 A | 7/1999 | Bolanos et al. |
| 5,928,157 A | 7/1999 | O'Dwyer |
| 5,931,764 A | 8/1999 | Freeman et al. |
| 5,970,921 A | 10/1999 | Fulton |
| 5,989,120 A | 11/1999 | Truchsess |
| 5,995,077 A | 11/1999 | Wilcox et al. |

(56) References Cited

U.S. PATENT DOCUMENTS

| | | | |
|---|---|---|---|
| 5,997,983 | A | 12/1999 | Caron et al. |
| 6,023,372 | A | 2/2000 | Spitzer et al. |
| 6,024,575 | A | 2/2000 | Ulrich |
| 6,026,512 | A | 2/2000 | Banks |
| 6,047,203 | A | 4/2000 | Sackner et al. |
| 6,080,690 | A | 6/2000 | Lebby et al. |
| 6,083,156 | A | 7/2000 | Lisiecki |
| 6,097,607 | A | 8/2000 | Carroll et al. |
| 6,105,624 | A | 8/2000 | Wildeman et al. |
| 6,117,554 | A | 9/2000 | Shalaby et al. |
| 6,121,171 | A | 9/2000 | Takahashi et al. |
| 6,121,547 | A | 9/2000 | Harada |
| 6,126,572 | A | 10/2000 | Smith |
| 6,128,004 | A | 10/2000 | McDowall et al. |
| 6,135,951 | A | 10/2000 | Richardson et al. |
| 6,145,551 | A | 11/2000 | Jayaraman et al. |
| 6,210,771 | B1 | 4/2001 | Post et al. |
| 6,231,516 | B1 | 5/2001 | Keilman et al. |
| 6,253,099 | B1 | 6/2001 | Oskin et al. |
| 6,254,548 | B1 | 7/2001 | Ishikawa et al. |
| 6,254,551 | B1 | 7/2001 | Varis |
| 6,270,466 | B1 | 8/2001 | Weinstein et al. |
| 6,277,080 | B1 | 8/2001 | Nissila et al. |
| 6,295,466 | B1 | 9/2001 | Ishikawa et al. |
| 6,315,009 | B1 | 11/2001 | Jayaraman et al. |
| 6,324,053 | B1 | 11/2001 | Kamijo |
| 6,325,066 | B1 | 12/2001 | Hughes et al. |
| 6,341,504 | B1 | 1/2002 | Istook |
| 6,341,550 | B1 | 1/2002 | White |
| 6,350,129 | B1 | 2/2002 | Gorlick |
| 6,381,482 | B1 | 4/2002 | Jayaraman et al. |
| 6,385,473 | B1 | 5/2002 | Haines et al. |
| 6,413,225 | B1 | 7/2002 | Sackner et al. |
| 6,416,471 | B1 | 7/2002 | Kumar et al. |
| 6,420,008 | B1 | 7/2002 | Lewis et al. |
| 6,445,940 | B1 | 9/2002 | Gevins et al. |
| 6,461,307 | B1 | 10/2002 | Kristbjarnarson et al. |
| 6,463,310 | B1 | 10/2002 | Swedlow et al. |
| 6,474,367 | B1 | 11/2002 | Jayaraman et al. |
| 6,493,933 | B1 | 12/2002 | Post et al. |
| 6,494,829 | B1 | 12/2002 | New, Jr. et al. |
| 6,496,695 | B1 | 12/2002 | Kouji et al. |
| 6,522,531 | B1 | 2/2003 | Quintana et al. |
| 6,527,711 | B1 | 3/2003 | Stivoric et al. |
| 6,551,252 | B2 | 4/2003 | Sackner et al. |
| 6,561,987 | B2 | 5/2003 | Pail |
| 6,677,858 | B1 | 1/2004 | Faris et al. |
| 6,687,523 | B1 | 2/2004 | Jayaraman et al. |
| 6,727,197 | B1 | 4/2004 | Wilson et al. |
| 6,729,025 | B2 | 5/2004 | Farrell et al. |
| 6,767,218 | B2 | 7/2004 | Marmaropoulos |
| 6,783,498 | B2 | 8/2004 | Sackner et al. |
| 6,785,144 | B1 | 8/2004 | Akram |
| 6,936,011 | B2 | 8/2005 | Sheldon |
| 6,941,775 | B2 | 9/2005 | Sharma |
| 6,970,731 | B1 | 11/2005 | Jayaraman et al. |
| 7,020,508 | B2 | 3/2006 | Stivoric et al. |
| 7,041,062 | B2 | 5/2006 | Friedrichs et al. |
| 7,076,291 | B2 | 7/2006 | Pulkkinen et al. |
| 7,092,846 | B2 | 8/2006 | Vock et al. |
| 7,319,895 | B2 | 1/2008 | Klefstad-Sillonville et al. |
| 7,559,902 | B2 | 7/2009 | Ting et al. |
| 7,618,260 | B2 | 11/2009 | Daniel et al. |
| 7,731,517 | B2 | 6/2010 | Lee et al. |
| 7,878,030 | B2 | 2/2011 | Burr |
| 8,029,300 | B2 | 10/2011 | Finney et al. |
| 8,086,421 | B2 | 12/2011 | Case et al. |
| 8,200,323 | B2 | 6/2012 | DiBenedetto et al. |
| 2002/0032388 | A1 | 3/2002 | Kristbjarnarson et al. |
| 2002/0044059 | A1 | 4/2002 | Reeder et al. |
| 2002/0107451 | A1 | 8/2002 | Pulkkinen et al. |
| 2002/0124295 | A1 | 9/2002 | Fenwick et al. |
| 2003/0139680 | A1 | 7/2003 | Sheldon |
| 2004/0092186 | A1 | 5/2004 | Wilson-Nguyen et al. |
| 2004/0097823 | A1 | 5/2004 | Friedrichs et al. |
| 2004/0209396 | A1 | 10/2004 | Krulevitch et al. |
| 2004/0224138 | A1 | 11/2004 | Farrell et al. |
| 2004/0225199 | A1 | 11/2004 | Evanyk et al. |
| 2005/0054941 | A1* | 3/2005 | Ting et al. ............... 600/529 |
| 2005/0119586 | A1 | 6/2005 | Coyle et al. |
| 2005/0240087 | A1 | 10/2005 | Keenan et al. |
| 2005/0282453 | A1* | 12/2005 | Jackson et al. ............... 442/249 |
| 2006/0009697 | A1 | 1/2006 | Banet et al. |
| 2006/0036142 | A1 | 2/2006 | Brister et al. |
| 2006/0117805 | A1 | 6/2006 | Valentine et al. |
| 2007/0115259 | A1 | 5/2007 | Pai |
| 2007/0299325 | A1 | 12/2007 | Farrell et al. |
| 2008/0000304 | A1* | 1/2008 | Nagle et al. ............... 73/780 |
| 2008/0139894 | A1* | 6/2008 | Szydlo-Moore et al. ..... 600/300 |
| 2008/0188353 | A1 | 8/2008 | Vitolo et al. |
| 2009/0190713 | A1 | 7/2009 | Wai |
| 2012/0029299 | A1 | 2/2012 | DeRemer et al. |
| 2012/0035426 | A1 | 2/2012 | Mielcarz et al. |
| 2012/0078127 | A1 | 3/2012 | McDonald et al. |

FOREIGN PATENT DOCUMENTS

| | | |
|---|---|---|
| EP | 1 064 963 A1 | 1/2001 |
| EP | 1 077 044 A1 | 2/2001 |
| EP | 1 164 815 A1 | 12/2001 |
| EP | 1 234 903 A1 | 8/2002 |
| EP | 1 328 137 A2 | 7/2003 |
| EP | 1 330 964 A2 | 7/2003 |
| EP | 1 339 259 A1 | 8/2003 |
| EP | 1 444 907 A1 | 8/2004 |
| EP | 1 269 502 B1 | 6/2005 |
| EP | 1 021 064 B1 | 9/2005 |
| EP | 1 049 354 B1 | 12/2005 |
| EP | 1 201 806 B1 | 12/2005 |
| FR | 2 836 050 A1 | 2/2003 |
| FR | 2858758 A2 | 8/2003 |
| GB | 2 143 135 A | 2/1985 |
| GB | 2 331 631 A | 2/1999 |
| GB | 2 336 514 A | 10/1999 |
| GB | 2 378 054 A | 1/2003 |
| GB | 2 385 277 A | 8/2003 |
| GB | 2 386 339 A | 9/2003 |
| GB | 2 396 256 A | 6/2004 |
| WO | WO 98/20200 | 5/1998 |
| WO | WO 99/19019 | 4/1999 |
| WO | WO 99/64657 | 12/1999 |
| WO | WO 00/25193 | 5/2000 |
| WO | WO 01/78577 A2 | 10/2001 |
| WO | WO 01/88935 | 11/2001 |
| WO | WO 02/07816 | 1/2002 |
| WO | WO 02/045538 A2 | 6/2002 |
| WO | WO 02/060370 A2 | 8/2002 |
| WO | WO 02/087929 A1 | 11/2002 |
| WO | WO 02/095839 A2 | 11/2002 |
| WO | WO 03/039417 A2 | 5/2003 |
| WO | WO 03/052541 A2 | 6/2003 |
| WO | WO 03/072861 A1 | 9/2003 |
| WO | WO 03/094717 A1 | 11/2003 |
| WO | WO 2004/053638 A2 | 6/2004 |
| WO | WO 2004/064108 A2 | 7/2004 |
| WO | WO 2004/091503 A2 | 10/2004 |
| WO | WO 2004/098703 A2 | 11/2004 |
| WO | WO 2004/107831 A2 | 12/2004 |
| WO | WO 2004/114401 A2 | 12/2004 |
| WO | WO 2005/000052 A1 | 1/2005 |
| WO | WO 2005/011415 A1 | 2/2005 |
| WO | WO 2005/013738 A2 | 2/2005 |

OTHER PUBLICATIONS

Gemperie, Francine, Kasabach, Chris, Stivoric, John, Bauer, Malcolm and Martin, Richard, *Design for Wearability*, Institute for Complex Engineered Systems, Carnegie Mellon University, Pittsburgh, PA http://www.ices.cmu.edu/design/weability, 1998 (7 pages).

(56) References Cited

OTHER PUBLICATIONS

"E-broidery: Design and Fabrication of Textile-based Computing", by E.R. Post et al., IBM Systems Journal, vol. 39, Nos. 3 & 4, 2000, pp. 840-860.

"Intrabody Buses for Data and Power", E. Rhemi Post et al., MIT Media Laboratory, 1997 IEEE, pp. 52-55.

E. Rehmi Post and Maggie Orth, Smart Fabric, or "Wearable Clothing", the MIT Media Laboratory, pp. 167-168 of the Digest of Papers of the First IEEE International Symposium on Wearable Computers, Oct. 13-14, 1997 held in Cambridge, Massachusetts.

"Wearable Sensor Badge & Sensor Jacket for Context Awareneess", Farringdon et al., Philips Research Laboratories, Surrey, U.K., 1999, IEEE pp. 107-113.

"Electronic Suspenders: A Fabric Power bus and Data Network for Wearable Digital Devices", Michael M. Gorlick, The Aerospace Corporation, El Segundo, California, 1999, IEEE, pp. 114-121.

Harper, Charles A., Handbook of Plastics, Elastomers, and Composites, Third Edition, McGraw-Hill, New York, 1996, pp. 6.14-6.19 (4 pages).

Neuman, Michael R., Biopotential Electrodes. The Biomedical Engineering Handbook, vol. 1, edited by Joseph D. Bronzino, CRC Press, Boca Raton, FL, 2000, pp. 48-1-48-12.

Post, E. Rhemi and Maggie Orth, Smart Fabric, or Washable Computing, the MIT Media Laboratory, Digest of Papers of the first IEEE International Symposium on Wearable Computers, Oct. 13-14, 1997 held in Cambridge, Massachusetts (4 pages).

Axisa, F. et al., "Flexible Technologies and Smart Clothing for Citizen, Medicine, Home Healthcare, and Disease Prevention", IEEE transactions on Information Technology in Biomedicine, vol. 9, No. 3, Sep. 2005, p. 325-336.

Pandiam, P.S. et al., "Wireless Sensor Network for Wearable Physiological Monitoring", Journal of Networks, vol. 3, No. 5, May 2008, p. 21-29.

\* cited by examiner

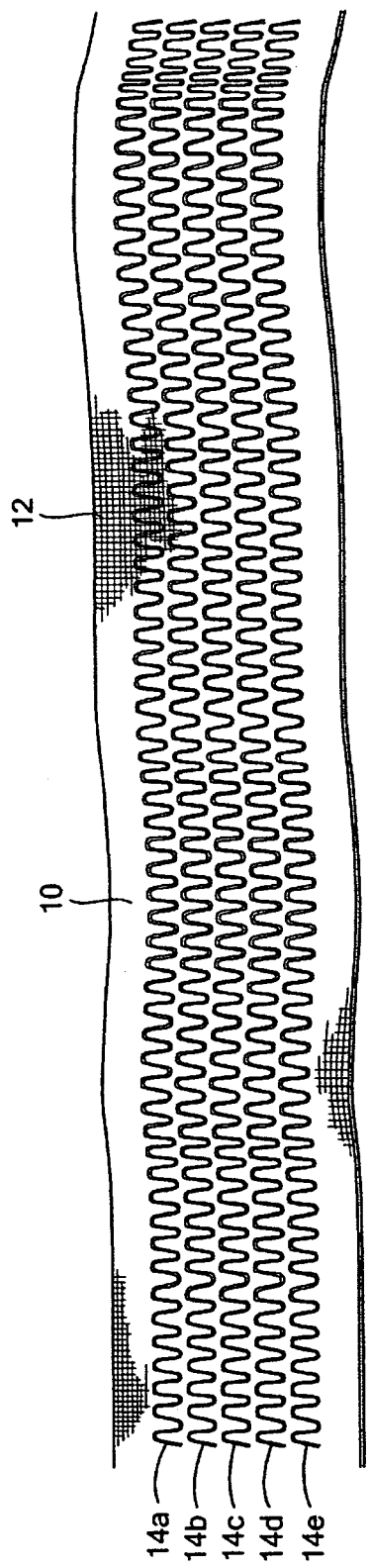
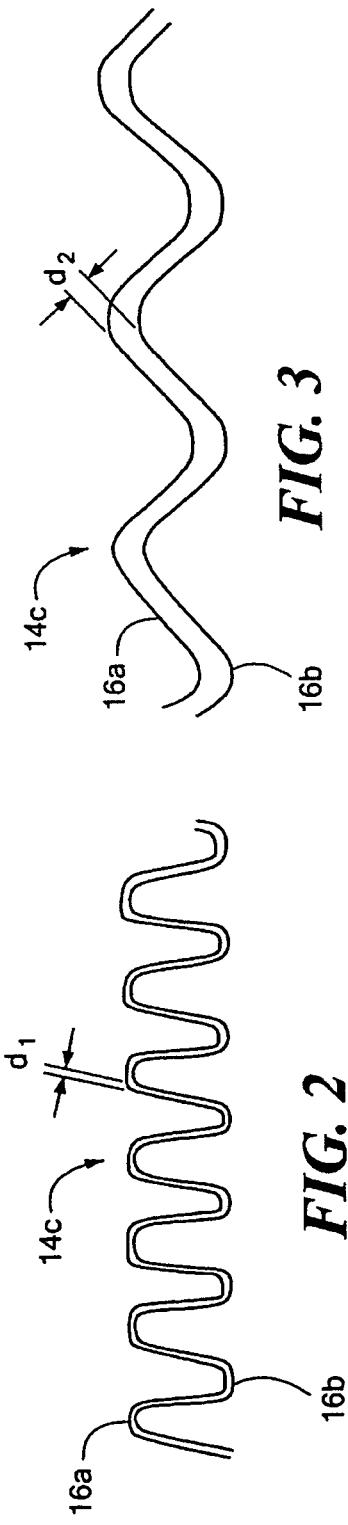
FIG. 1
FIG. 2
FIG. 3

RESPIRATION SENSING SYSTEM

GOVERNMENT RIGHTS

Certain aspects of this invention were made with U.S. Government support under Contract No. W81XWH-04-1-0146 with the Army. The Government may have certain rights in the subject invention.

RELATED APPLICATIONS

This application is related to U.S. patent application Ser. No. 11/807,449, filed on May 29, 2007 and U.S. patent application Ser. No. 10/922,336, filed Aug. 20, 2004, both of which are incorporated herein by reference.

FIELD OF THE INVENTION

The subject invention relates to a physiological monitoring system able to monitor and record a subject's respiration rate.

BACKGROUND OF THE INVENTION

Various systems are known which monitor a person's heart rate, respiration rate, body temperature, and the like. For ambulatory-type systems, a portable unit may be used to wirelessly transmit the various sensor signals to a base station computer for processing, display, and storage.

For sport, outdoor, and military applications especially, the portable unit must be waterproof and removable from the shirt or garment carrying the sensors in order to wash the shirt or garment. The electrical connections between the sensors and the portable unit must be robust. And yet, no system will be commercially viable if numerous manual labor steps are required increasing manufacturing costs. The portable unit must be small, remain electrically connected to the sensors while in use, and not interfere with the activity being carried out by the user.

Several wearable physiological monitoring systems have been proposed. They typically include one or more sensors (e.g., a respiration sensor, a heart rate sensor, an accelerometer, and the like). Using a transmitter, the sensed data is transmitted to a base/readout unit. Some prior art references disclose a sensor subsystem with a transmitter apparently hard wired to the sensors. See, e.g., U.S. Published Patent Application No. 2005/0240087 and U.S. Pat. No. 6,416,471, incorporated herein by this reference.

Other prior art references disclose a stand alone sensor/transmitter unit carried by the user. See, e.g., U.S. Pat. No. 7,092,846. Such systems cannot sense respiration, heart rate, and the like. The APPLE+NIKE product, now on the market, is similar.

For sports, military, and other applications where the sensor subsystem is integrated into a shirt or other garment, the garment is typically washed between uses. Also, when worn, it is important that nothing interfere with the user's comfort. Some physiological monitoring systems are not comfortable to wear; others are difficult to use. Some require preparation prior to and/or after donning the garment. Some include discrete wires which must be routed and/or connected each time the garment is worn. Some include electrodes which must be secured to the person's body and/or must be used in connection with a conductive gel. Some physiological monitoring garments are simply not aesthetically pleasing. Others interfere with the activities of and duties carried out by the wearer.

Respiration can be sensed in a couple of different ways. See U.S. Pat. Nos. 4,815,473; 5,301,678; 6,047,203 incorporated herein by this reference. One respiration sensing subsystem includes a flexible band with a pair of spaced conductors extending along the band in a flexible configuration. The band is fitted about the person's chest and, as the person inhales and exhales, the distance between the two conductors changes. This change in distance between the two conductors can be sensed to provide respiration data. See U.S. Pat. No. 7,559,902, incorporated herein by this reference.

In non ambulatory, non-athletic uses, such respiration sensing subsystems function adequately. When the applicant began testing such systems on athletes, soldiers, and for use in other ambulatory environment, however, the detected respiration rate of the subject slowly went down to zero even though it was clear that the subjects were still breathing.

BRIEF SUMMARY OF THE INVENTION

An analysis of the situation by the inventors revealed that sweat, soaking the stretchable band, may become shorted electrically to the circuit via other sensors or electrical pathways in the system. In general, the dielectric between the conductor pair varied from air to a mixture of salt and water as the user sweats. Sweat is electrically conductive and provided a pathway for a short. The result was an undesirable variation in the range of measured capacitance values resulting in inaccurate calculations of breath rate.

In one aspect of the subject invention, a more reliable respiration sensor is provided. The respiration sensor can be used to monitor the respiration rate of athletes, soldiers, and others in ambulatory environments. The subject invention results from the realization, in part, that, in one example, a more reliable respiration sensor includes just enough flexible silicone worked into the material of the stretchable band between the two conductors used to detect respiration to serve as a dielectric between the conductor pair to prevent moisture from penetrating the material of the stretchable band and affecting the measurement of respiration. Excess silicone which would adversely affect the stretchability of the band is avoided.

The subject invention features a respiration sensing subsystem comprising a band made of stretchable material, a pair of spaced conductors extending along the band in a flexible pattern, and a moisture repellant compound in the stretchable material of the band between the pair of spaced conductors serving as a dielectric between the conductor pair. In one version, the conductors are insulated wire incorporated (e.g., woven) into the band and the moisture repellant compound includes silicone.

The subject invention also features a method of making a respiration sensing subsystem. On preferred method includes integrating a pair of spaced conductors in a flexible pattern into the material of a stretchable band. Changes in impedance between the spaced conductors are detected as the band stretches in order to sense at least one respiration parameter. A moisture repellant compound is incorporated into the stretchable material of the band between the pair of spaced conductors to prevent the moisture from affecting the sensing of said at least one parameter.

One respiration sensing subsystem in accordance with the subject invention features a band made of stretchable material and spaced insulated wires woven into the band extending along the band in a flexible pattern. At least one pair of insulated wires serve to sense respiration. A moisture repellant compound is integrated in the stretchable material of the band between the pair of insulated wires serving to sense respiration.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which:

FIG. 1 is a schematic front view of a respiration subsystem stretchable band in accordance with the subject invention;

FIG. 2 is a schematic depiction of two conductors integrated into the band shown in FIG. 1 when the band is in a relaxed state;

FIG. 3 is a schematic depiction of the two conductors shown in FIG. 2 when the band of FIG. 1 is in an expanded state;

DETAILED DESCRIPTION OF THE INVENTION

Figure 5:
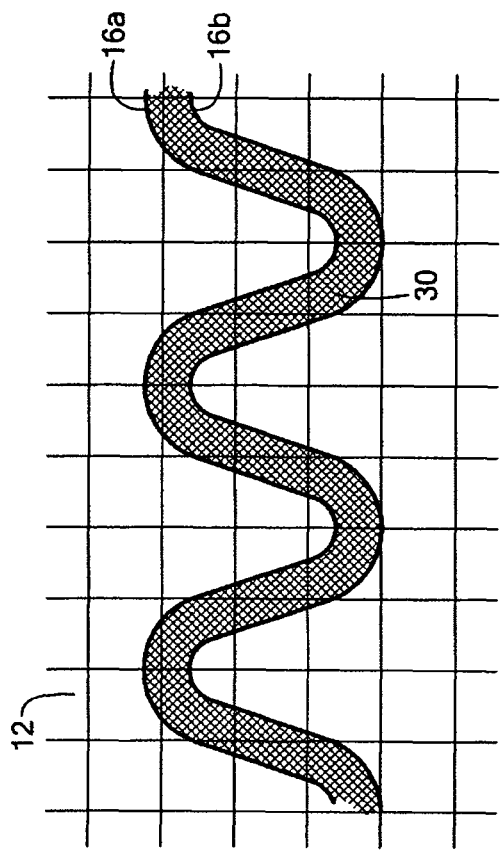
FIG. 5 is a highly schematic depiction of a stretchable band fabricated in accordance with the method depicted in FIG. 4.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

FIG. 1 shows stretchable band 10 and integrated (e.g., woven) with the fabric 12 (e.g., a polyester and nylon blend) of band 10 are conductors (typically insulated wires) in a flexible configuration typically in-plane nested pairs as shown at 14a-14e. Each wire may be about 0.022 inches in diameter. The nested pairs may be sinusoidal as shown, or in any other suitable flexible configuration such as a triangle wave or zig-zag. One conductor pair 14c is shown more clearly in FIGS. 2-3 and can be used as a component of a respiration sensing subsystem in accordance with the subject invention. When the band is relaxed because the wearer has exhaled, the distance between wires 16a and 16b is $d_1$, FIG. 2. When the band is stretch because the wearer has inhaled, the distance between wires 16a and 16b is $d_2$ as shown in FIG. 3. In this way, by configuring in the band to be circumferential about the wearer's chest and snug thereabout in the relaxed configuration, when the wearer breaths, any nested conductor pair in the band can be used as a respiration detector. See Published U.S. Patent Application No. 2007/0299325, incorporated herein by this reference.

An electronics module includes a circuit which detects changes in impedance, preferably capacitance but also perhaps inductance, as the adjacent nested circumferential conductors move away from and towards each other as stretchable band 10, FIG. 1 expands and contracts as shown in FIGS. 2-3. That change in impedance is thus indicative of respiration, indicating frequency of breaths taken by the wearer, as well as, in some examples, the depth or volume of each breath. In a plot of impedance over time, peak to peak distance is indicative of breathing rate or frequency.

Other conductor pairs can also be used for sensing respiration but typically at least a few conductors are reserved for signal transmissions from a sensor, such as an ECG electrode, to an electronics module or portable transmitting unit and possibly between the electronics module and these and other sensors which may be included on or electrically connected to the band. The other conductors can be used to route electrical signals from other sensors and the like to a portable transmitting unit connected to band 10, FIG. 1.

As discussed in the Background Section above, when moisture permeates the material 12 of band 10 between conductor pair 16a and 16b, FIGS. 2-3, the respiration rate of the wearer can no longer be reliably detected.

Figure 6:
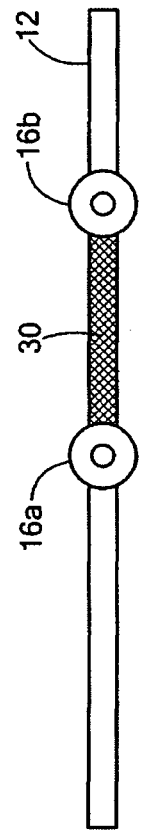
FIG. 6 is a cross-sectional view of the band shown in FIG. 5.
Figure 4:
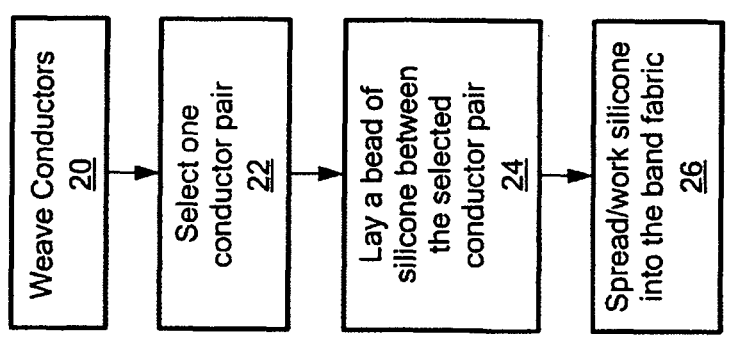
FIG. 4 is a flow chart depicting the primary steps associated with a method of manufacturing of a respiration sensing subsystem in accordance with the subject invention.

In accordance with one aspect of the subject invention, this problem was solved as follows. As discussed above, conductor pairs 16a and 16b are woven into the fabric of the stretchable band, step 20, FIG. 4. One pair of conductors is selected to serve as a component of a respiration sensing subsystem, step 22. Typically, the pair of wires is about 0.10 inches apart when the band is in its relaxed configuration. A bead of a moisture repellant material such as flexible silicone is laid between the selected pair of wires, step 24. In step 26, a small tool with a head about 0.4 inches across is used to spread the silicone bead into the fabric material of the band between the two wires and typically through the thickness of the band of material as shown in FIGS. 5 and 6 where the fabric band is shown at 12, wires 16a and 16b are shown woven into the fabric of the band, and silicone material 30 is shown permeating fabric 12 front to back between wires 16a and 16b. A suitable silicone compound is Dow 734. Curing can occur at room temperature or using UV lamps.

When the user sweats, moisture may permeate fabric 12 but silicone material 30 sheds moisture and prevents moisture from affecting the respiration measurements as the distance between wires 16a and 16b changes as described above.

Instead of air, or a combination of water and salt (when the wearer sweats) serving as the dielectric between two adjacent conductors in the band, the flexible moisture repellant compound now serves as the dielectric between the two adjacent conductors in the band. The surprising result is a reduced dynamic range of capacitance values measured as the system is used. The result is more reliable respiration measurements.

In the prior art, the dielectric between the conductor pair is first air and then changes to a water/salt mixture which can short the conductor pair. In any case, since the dielectric changed, the dynamic range of capacitance values measured was substantial Care should be taken to avoid excess silicone material since the stretchability of band material 12 would be adversely affected if too much silicone is used. It is generally not desirable, for example, for silicone material to be impregnated across the entire extent of band 10, FIG. 1. Silicone is not required for example, between conductor pairs 14a, 14b, 14d, or 14e if these conductors are not used to detect respiration. Instead, in the best mode, silicone is impregnated into the band material only between the two conductors chosen to serve as the components of a respiration sensing subsystem. The result, in one preferred embodiment, is a more reliable respiration sensor which can be used to monitor the respiration rate of athletes, soldiers, and others in ambulatory environments.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A respiration sensing subsystem comprising:
   a band made of stretchable material;
   a pair of adjacent spaced conductors extending along the band in a flexible pattern serving as components of the respiration sensing subsystem; and
   a flexible moisture repellant compound permeating the band front to back in the stretchable material of the band between the pair of adjacent spaced conductors only, said compound serving as a dielectric material between the spaced conductors for measuring respiration as the band stretches and impedance between the conductors varies.

2. The respiration sensing subsystem of claim 1 in which the conductors are insulated wire integrated into the band.

3. The respiration sensing subsystem of claim 1 in which the flexible moisture repellant compound includes silicone.

4. The respiration sensing subsystem of claim 1 in which the band is made of a stretchable fabric material.

5. A respiration sensing subsystem comprising:
   a band made of stretchable material;
   a pair of adjacent spaced conductors extending along the band in a flexible pattern serving as components of the respiration sensing subsystem; and
   a flexible moisture repellant compound impregnated into and permeating the band front to back in the stretchable material of the band between the pair of adjacent spaced conductors only to avoid adverse affects on stretchability of the band, said compound serving as a dielectric material between the spaced conductors for measuring respiration and for reducing dynamic range of measured values as the band stretches and impedance between the conductors varies.

6. A respiration sensing subsystem comprising:
   a band made of stretchable material;
   a pair of adjacent spaced insulated conductors extending along the band in a flexible pattern serving as components of the respiration sensing subsystem; and
   a flexible moisture repellant compound between said spaced insulated conductors serving as the dielectric between said conductors instead of air.

* * * * *